(12) United States Patent
Kang et al.

(10) Patent No.: US 10,209,213 B2
(45) Date of Patent: Feb. 19, 2019

(54) FLEXIBLE SENSOR PATCH AND METHOD OF USING THE SAME

(71) Applicant: 3M INNOVATIVE PROPERTIES COMPANY, St. Paul, MN (US)

(72) Inventors: Myungchan Kang, Woodbury, MN (US); Stefan H. Gryska, Woodbury, MN (US); Michael C. Palazzotto, Woodbury, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 0 days.

(21) Appl. No.: 15/121,278

(22) PCT Filed: Feb. 19, 2015

(86) PCT No.: PCT/US2015/016624
§ 371 (c)(1),
(2) Date: Aug. 24, 2016

(87) PCT Pub. No.: WO2015/130550
PCT Pub. Date: Sep. 3, 2015

(65) Prior Publication Data
US 2016/0363555 A1 Dec. 15, 2016

Related U.S. Application Data

(60) Provisional application No. 61/945,600, filed on Feb. 27, 2014.

(51) Int. Cl.
*G01N 27/22* (2006.01)
*G01N 27/407* (2006.01)
*A61B 46/20* (2016.01)

(52) U.S. Cl.
CPC ........... *G01N 27/227* (2013.01); *A61B 46/20* (2016.02); *G01N 27/22* (2013.01); *G01N 27/228* (2013.01);
(Continued)

(58) Field of Classification Search
CPC .. G01N 27/227; G01N 27/228; G01N 27/407; G01N 27/22
(Continued)

(56) References Cited

U.S. PATENT DOCUMENTS

RE24,906 E 12/1960 Ulrich
3,389,827 A 6/1968 Abere
(Continued)

FOREIGN PATENT DOCUMENTS

EP 035399 9/1981
EP 051935 5/1982
(Continued)

OTHER PUBLICATIONS

Ataman, "A Robust Platform for Textile Integrated Gas Sensors," Sensors and Actuators B: Chemical, Feb. 2013, vol. 177, pp. 1053-1061.
(Continued)

*Primary Examiner* — Amy He
(74) *Attorney, Agent, or Firm* — Yufeng Dong

(57) ABSTRACT

A flexible sensor patch includes a flexible base having outer and inner surfaces and a periphery, an adhesive layer disposed on at least a portion of the outer surface, a flexible porous cover secured to the flexible base along at least major portion of the periphery. The flexible porous cover and the flexible base collectively enclose at least a major portion of a sensor. The sensor comprises a capacitive sensor element. The capacitive sensor element comprises first and second conductive electrodes and a dielectric microporous material disposed therebetween. Methods of using the flexible sensor patch are also disclosed.

13 Claims, 4 Drawing Sheets

(52) U.S. Cl.
CPC ...... *G01N 27/407* (2013.01); *A61B 2046/205* (2016.02)

(58) Field of Classification Search
USPC .............................. 324/663, 667, 686, 658
See application file for complete search history.

(56) References Cited

U.S. PATENT DOCUMENTS

| | | | |
|---|---|---|---|
| 4,112,213 A | 9/1978 | Waldman | |
| 4,310,509 A | 1/1982 | Berglund | |
| 4,323,557 A | 4/1982 | Rosso | |
| 4,737,410 A | 4/1988 | Kantner | |
| 5,531,855 A | 7/1996 | Heinecke | |
| 5,614,310 A | 3/1997 | Delgado | |
| 5,849,325 A | 12/1998 | Heinecke | |
| 6,372,323 B1 * | 4/2002 | Kobe | A63B 49/08 24/442 |
| 6,566,575 B1 * | 5/2003 | Stickels | A61F 13/023 602/41 |
| 7,456,744 B2 | 11/2008 | Kuhns | |
| 7,498,802 B2 | 3/2009 | Takahata | |
| 7,948,380 B2 | 5/2011 | Kuhns | |
| 2006/0246273 A1 | 11/2006 | McKeown | |
| 2007/0215709 A1 | 9/2007 | Baude | |
| 2008/0018424 A1 | 1/2008 | Takahata | |
| 2009/0009193 A1 | 1/2009 | Hsiung | |
| 2011/0031983 A1 * | 2/2011 | David | G01N 27/125 324/663 |
| 2011/0045601 A1 | 2/2011 | Gryska | |
| 2013/0229194 A1 | 9/2013 | Palazzotto | |

FOREIGN PATENT DOCUMENTS

| | | |
|---|---|---|
| EP | 2275805 | 1/2011 |
| GB | 1280631 | 7/1972 |
| WO | WO 89/04630 A1 | 6/1989 |
| WO | WO 2005-012397 | 2/2005 |
| WO | WO 2008-008643 | 1/2008 |
| WO | WO 2009-045733 | 4/2009 |
| WO | WO 2009/046011 A2 | 4/2009 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2015-047750 | 4/2015 |

OTHER PUBLICATIONS

Budd, "Free Volume and Intrinsic Microporosity in Polymers," Journal of Materials Chemistry, Feb. 2005, vol. 15, pp. 1977-1986.
Budd, "Polymers of Intrinsic Microporosity (PIMs): Robust, Solution-Processable, Organic Nanoporous Materials," Chemical Communications, 2004, pp. 230-231.
Budd, "Solution-Processed, Organophilic Membrane Derived from a Polymer of Intrinsic Microporosity," Advanced Materials, Mar. 2004, vol. 16, No. 5, pp. 456-459.
Carta, "Novel Spirobisindanes for Use as Precursors to Polymers of Intrinsic Microporosity," Organic Letters, 2008, vol. 10, No. 13, pp. 2641-2643.
Foucaran, "Porous Silicon Layer Coupled With Thermoelectric Cooler: A Humidity Sensor," Sensors and Actuators A: Physical, Feb. 2000, vol. 79, No. 3, pp. 189-193.
Ghanem, "High-Performance Membranes from Polyimides with Intrinsic Microporosity," Advanced Materials, Jul. 2008, vol. 20, No. 14, pp. 2766-2771.
Ghanem, "Polymers of Intrinsic Microporosity Derived from Bis(phenazyl) Monomers," Macromolecules, Mar. 2008, vol. 41, No. 5, pp. 1640-1646.
Lorwongtragool, A Zigbee-Based Wireless Wearable Electronic Nose Using Flexible Printed Sensor Array, IEEE 5$^{th}$ International Nanoelectronics Conference (INEC), Jan. 2013, pp. 291-293.
McKeown, "Polymers of Intrinsic Microporosity (PIMs): Bridging the Void between Microporous and Polymeric Materials," Chemistry-A European Journal, Apr. 2005, vol. 11, No. 9, pp. 2610-2620.
Potyrailo, "Multianalyte Chemical Identification and Quantitation Using a Single Radio Frequency Identification Sensor," Analytical Chemistry, Jan. 2007, vol. 79, No. 1, pp. 45-51.
Zampetti, "Flexible Sensorial System Based on Capacitive Chemical Sensors Integrated With Readout Circuits Fully Fabricated on Ultra-Thin Substrate," Sensors and Actuators B: Chemical, Jul. 2011, vol. 155, No. 2, pp. 768-774.
International Search Report for PCT International Application No. PCT/US2015/016624, dated Apr. 30, 2015, 4 pages.

* cited by examiner

FLEXIBLE SENSOR PATCH AND METHOD OF USING THE SAME

CROSS REFERENCE TO RELATED APPLICATIONS

This application is a national stage filing under 35 U.S.C. 371 of PCT/US2015/016624, filed Feb. 19, 2015, which claims the benefit of U.S. Application No. 61/945,600, filed Feb. 27, 2014, the disclosure of which is incorporated by reference in its/their entirety herein.

TECHNICAL FIELD

The present disclosure broadly relates to vapor sensors and methods of using them.

BACKGROUND

The presence of vapors, and their concentration in air, is monitored in many fields of endeavor. Various methods for detecting vapors (e.g., volatile organic compounds (VOCs)) have been developed including, for example, photoionization, gas chromatography, gravimetric techniques, spectroscopic techniques (e.g., mass spectrometry, infrared spectroscopy, or fluorescence spectroscopy), and absorptive sensing techniques.

In capacitance sensors, the capacitance of two conductive electrodes (typically parallel or interdigitated), varies as the dielectric constant of material between the two electrodes changes due to the presence of an environmental analyte vapor.

Conventional capacitance sensors are typically complex mechanical devices in which a sensor is disposed within a rigid housing. However, such devices can be expensive to make, and may not be well-suited for applications in which they need to be mounted to an uneven and/or curved surface.

SUMMARY

In one aspect, the present disclosure provides a flexible sensor patch comprising:
  a flexible base having outer and inner surfaces and a periphery;
  an adhesive layer disposed on at least a portion of the outer surface;
  a sensor comprising a capacitive sensor element, the capacitive sensor element comprising:
    a first conductive electrode;
    a second conductive electrode; and
    a dielectric microporous material disposed between the first and second conductive electrodes; and
  a flexible porous cover secured to the flexible base along at least major portion of the periphery, wherein the flexible porous cover and the flexible base collectively enclose at least a major portion of the sensor.

In another aspect, the present disclosure provides a method of monitoring organic vapor concentration proximate to a substrate, the method comprising:
  providing a flexible sensor patch according to the present disclosure,
  adhesively bonding the adhesive layer to a substrate;
  establishing a voltage difference between the first and second conductive electrodes; and
  obtaining a capacitance-related property of the sensor.

Advantageously, sensor according to the present disclosure may be inexpensively fabricated, making them suitable for use as a disposable sensor. Due to their flexibility they are suitable for mounting on curved and/or uneven surfaces including, for example, pipes and animal skin. In one use, the flexible sensor patch can be adhered to a pre-surgical patient to monitor alcohol residue from sterilization procedures at a surgical site prior to application of a surgical drape. Ensuring that alcohol concentration is sufficiently low may help assure that adhesive on the surgical drape will adhere securely to the patient skin during surgery.

Features and advantages of the present disclosure will be further understood upon consideration of the detailed description as well as the appended claims.

Figure 1A:
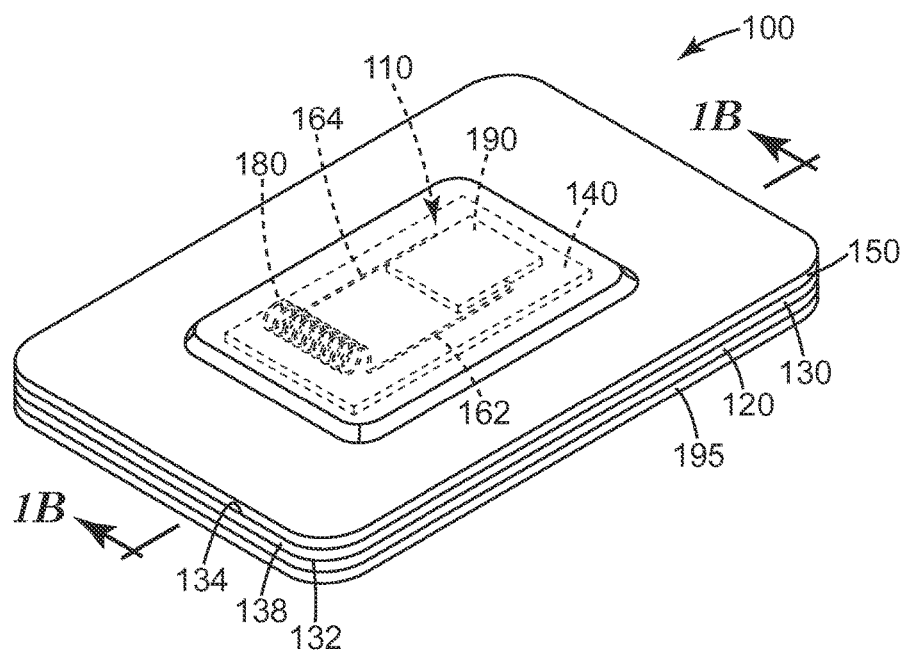
FIG. 1A is a schematic perspective view of an exemplary flexible sensor patch 100 according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figure may not be drawn to scale.

DETAILED DESCRIPTION

Figure 1B:
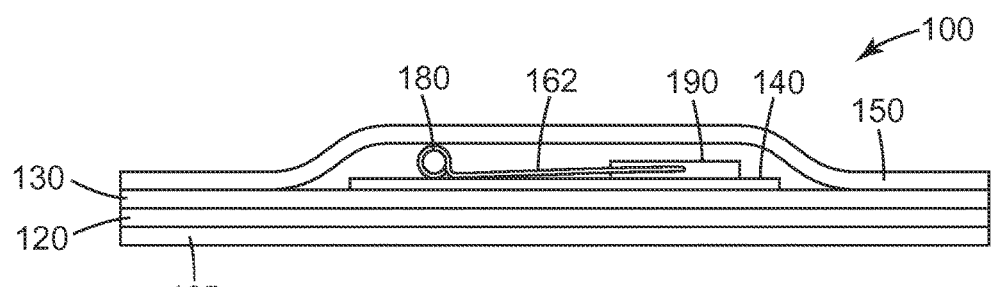
FIG. 1B is a schematic cross-sectional side view of flexible sensor patch 100 shown in FIG. 1A taken along line 1B-1B.

Referring now to FIGS. 1A and 1B, exemplary flexible sensor patch 100 comprises: flexible base 130 having outer and inner surfaces 132, 134 and a periphery 138; adhesive layer 120 disposed on at least a portion of the outer surface 134; sensor 110; and flexible porous cover 150 secured to flexible base 130 along at least major portion of periphery 138. Adhesive layer 120 is disposed on optional release layer 195. Flexible porous cover 150 and flexible base 130 collectively fully enclose sensor 110. Sensor 110 comprises capacitive sensor element 190 and radiofrequency transponder 180 electrically coupled in series with capacitive sensor element 190 through wires 162, 164. Radiofrequency transponder 180 and capacitive sensor element 190 are supported on optional dielectric sensor base 140.

Figure 2A:
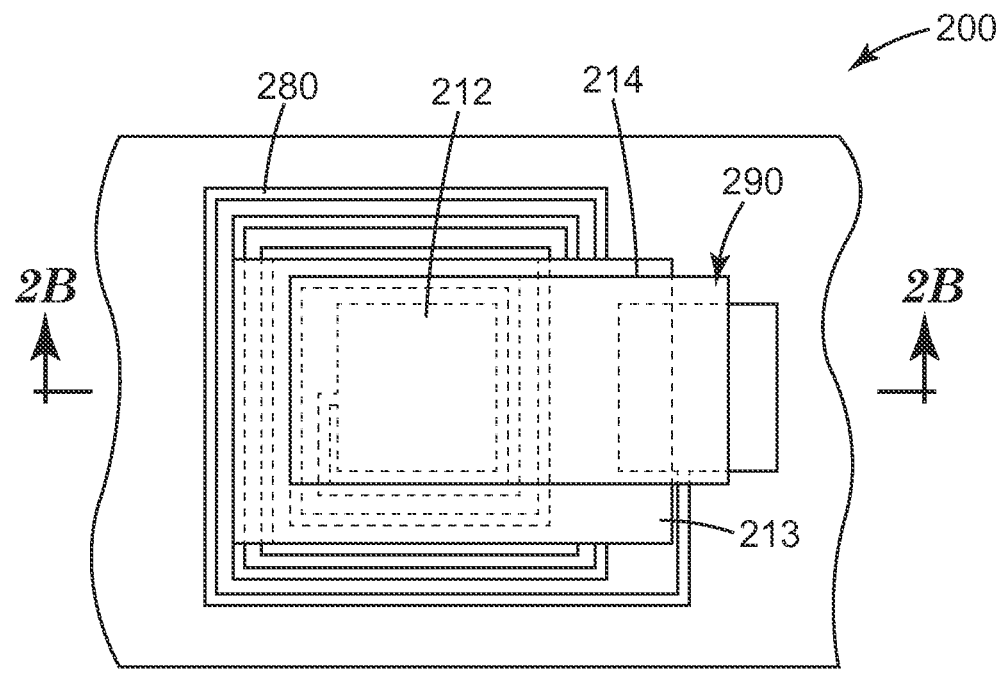
FIG. 2A is a schematic plan view of exemplary sensor 200.
Figure 2B:
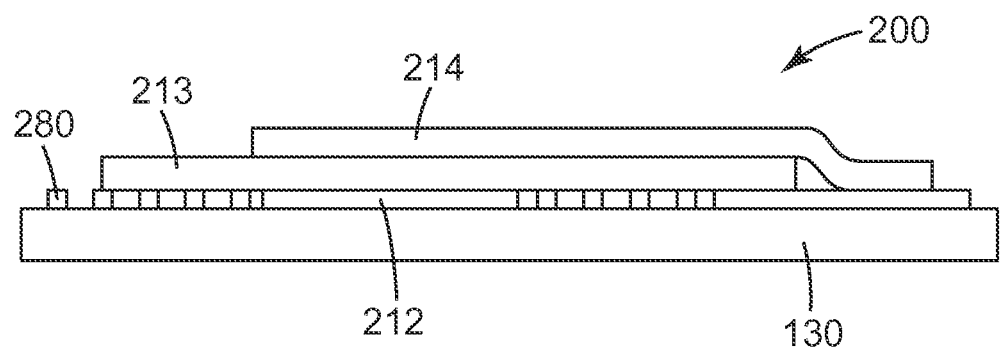
FIG. 2B is a schematic cross-sectional view of exemplary sensor 200 taken along line 2B-2B

FIGS. 2A and 2B show an exemplary sensor 200 that may be used in place of sensor 110 in the flexible sensor patch 100 construction shown in FIGS. 1A and 1B. Referring now to FIGS. 2A and 2B, sensor 200 includes radiofrequency transponder 280 and capacitive sensor element 290 formed directly on flexible base 130. Dielectric microporous material 213 is disposed between first conductive electrode 212 and second conductive electrode 214.

Radiofrequency transponders and methods of their fabrication are well known; for example, in the radiofrequency identification (RFID) and are widely available from commercial sources. Exemplary useful RF transponders include planar loop antennae and wound wire coils.

Useful adhesive layers may comprise any adhesive material such as, for example, a pressure-sensitive adhesive (PSA), a hot-melt adhesive, or a thermosetting adhesive. Preferably, the adhesive comprises, consists essentially of, or even consists of pressure-sensitive adhesive. For applications in which the adhesive layer would contact human skin (e.g., monitoring alcohol concentration at a pre-surgical site), the adhesive layer should be suitable for direct patient (e.g., human or animal) skin contact. Any PSA may be used, although for skin contact applications the adhesives are of the class known as "hypoallergenic" pressure-sensitive adhesives. Examples of some useful adhesives include acrylate copolymers described in U.S. Pat. No. RE 24,906 (Ulrich), particularly a 97:3 isooctyl acrylate:acrylamide copolymer. Also useful is an 70:15:15 isooctyl acrylate:ethylene oxide acrylate:acrylic acid terpolymer, as described in U.S. Pat. No. 4,737,410 (Kantner et al.). Still other useful adhesives are described in U.S. Pat. No. 3,389,827 (Abere et al.); U.S. Pat. No. 4,112,213 (Waldman); U.S. Pat. No. 4,310,509 (Berglund et al.); and 4,323,557 (Rosso et al.); U.S. Pat. No. 5,614,310 (Delgado et al.); U.S. Pat. No. 5,849,325 (Heinecke et al.); as well as U.K. Pat. No. 1280631 (Seymour) and European Pat. Nos. 35399 B1 (Peck) and 51935 B1 (Heinecke).

The adhesive layer may be protected by lamination to a release liner that is disposed on the adhesive layer opposite the flexible base. Release liners generally include a backing, optionally having a low adhesion (with respect to the adhesive layer) coating thereon. Exemplary release liners include siliconized papers and polymer films (e.g., polyethylene and/or polypropylene) optionally having a low energy coating (fluoropolymer of silicone) thereon. One useful release liner may be preferably coated on a backing as a solution of polyvinyl N-octadecyl carbamate and a blend of silicone resins, as described in, e.g., U.S. Pat. No. 5,531,855 (Heinecke et al.).

The flexible porous cover is first of all flexible and porous. As used herein, the term "flexible" means capable of being bent, preferably easily bent, repeatedly without injury or damage. As used herein, the term "porous" in reference to a thing or material means having sufficient porosity that organic vapor can diffuse through it in the gaseous state.

Porosity may be achieved through one or more perforations and/or through innate permeability of the porous cover to an analyte vapor (e.g., ethanol vapor). Any suitable material may be used for the flexible porous cover. Examples include flexible porous polymer films (e.g., a transparent, semi-permeable and virtually non-adherent soft nylon material available under the trade designation "TEGADERM" from 3M Company, St. Paul, Minn.), papers, and flexible porous fabrics. Useful fabrics include woven or knitted fabrics, and nonwoven fabrics (e.g., air-laid, melt-blown, wet-laid, spun-laced, and/or melt-spun fabrics). Examples nonwoven fabrics comprising polyolefin fibers such as, e.g., polyethylene and/or polypropylene fibers, polyamide fibers, polyester fibers, polyurethane fibers, acrylic fibers, and combinations thereof.

The flexible base may comprise any material that is flexible and capable of supporting the adhesive layer and bonding to the flexible porous cover. In certain embodiments, the flexible base is dielectric, although this is not a requirement. Examples of suitable materials for the flexible base include polymer films comprising, polyethylene, polypropylene, polyacetals, engineering plastics (e.g., polyamides, polyethylene terephthalate(PET), polyimides, polycarbonates, polyetheretherketone (PEEK), and polyetherketone (PEK)), and combinations thereof, fabric (e.g., woven, knitted, or nonwoven fabric), paper, and combinations thereof. Preferably, the flexible base is dielectric, although this is not a requirement.

Referring again to FIG. 1, the radiofrequency transponder 180 electrically coupled in series with capacitive sensor element 190 enables the sensor to be read using radiofrequency interrogation techniques, with varying signal depending on the capacitance of the sensor element as it changes due to adsorption/absorption of analyte vapor.

The capacitive sensor element comprises a first conductive electrode, a second conductive electrode, and a dielectric microporous material disposed between (in some embodiments, sandwiched between) the first and second conductive electrodes.

The dielectric microporous material is dielectric and microporous. In this context, the terms "microporous" and "microporosity" mean that the material has a significant amount of internal, interconnected pore volume, with the mean pore size (as characterized, for example, by sorption isotherm procedures) being less than about 100 nanometers (nm), typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

In some embodiments, the microporous material comprises a so-called Polymer of Intrinsic Microporosity (PIM). PIMs are polymeric materials with nanometer-scale pores due to inefficient packing of the polymer chains. For example, in *Chemical Communications*, 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1 (below).

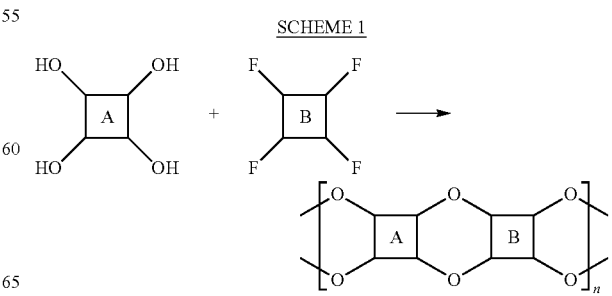

SCHEME 1

TABLE 1

| COMPONENT A | COMPONENT B |
|---|---|
| 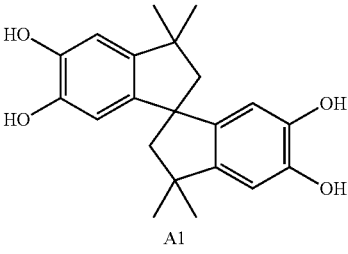<br>A1 | 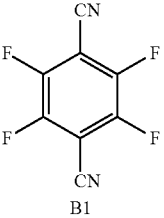<br>B1 |
| 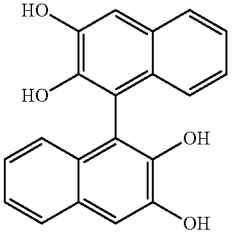<br>A2 | 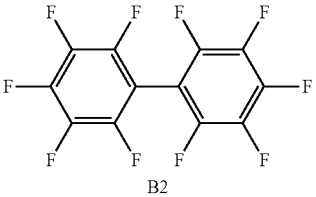<br>B2 |
| 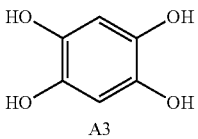<br>A3 | 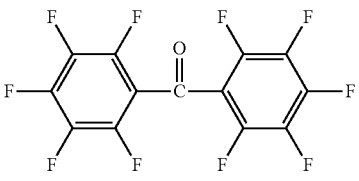<br>B3 |

Further suitable components A and B, and resultant intrinsically microporous polymers, are known in the art; for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Pat. Appl. Publ. No. 2006/0246273 A1 (McKeown et al. Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

In addition to solution coating methods, the dielectric microporous material may be applied to the either of the first or second conductive electrodes, or to the optional dielectric base by any other suitable method.

The dielectric microporous material may comprise a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Suitable dielectric bases can comprise any material capable of supporting the first conductive electrode and optionally the second conductive material and dielectric microporous material. The dielectric base may be a continuous slab, layer, or film of material. If present, it is disposed in sufficient proximity to the first conductive electrode that it may serve to provide physical strength and integrity to the sensor element. The dielectric base need not physically contact the first conductive electrode, although this is typically preferable. Any solid material having structural integrity, flexible or rigid, may be used as long as it does not interfere with operation of the sensor element. Suitable dielectric materials that may be used for the dielectric base include, for example, glass, ceramic, and/or plastic. In some embodiments, the substrate has a flat major surface on which the first conductive electrode is disposed. In large-scale production, a polymeric film (such as polyester or polyimide) may be advantageously used.

When a differential voltage is applied across the first and second conductive electrodes, the sensor element functions as a variable capacitor, the capacitance of which changes as a function of the dielectric constant of the dielectric detection material. As the dielectric microporous material contacts an analyte vapor (e.g., an organic analyte vapor), the analyte vapor is adsorbed and/or absorbed in the pores of the dielectric microporous material causing a change in its dielectric constant.

The first conductive electrode can comprise any suitable electrically conductive, and preferably thermally conductive material. Combinations of different materials (conductive and/or nonconductive) can be used, as different layers or as a mixture, as long as sufficient overall electrical conductivity is provided. The first conductive electrode need not be permeable to the analyte vapor to be detected, however this is not a requirement. Typically, the first conductive electrode has a sheet resistance of less than about $10^7$ ohms/square. Examples of materials that can be used to make the first conductive electrode include, but are not limited to, organic materials, inorganic materials, metals, alloys, and various mixtures and composites comprising any or all of these materials. In certain embodiments, coated (for example, thermal vapor coated, or sputter coated) metals or metal oxides, or combinations thereof, may be used. Suitable conductive materials include for example aluminum, nickel, titanium, tin, indium-tin oxide, gold, silver, platinum, palladium, copper, chromium, and combinations thereof.

The first conductive electrode can be of any thickness as long as it is conductive; for example, it may have a thickness in a range of from at least 4 nanometers (nm) to 1000 nm, or from 10 nm to 200 nm.

Figure 3:
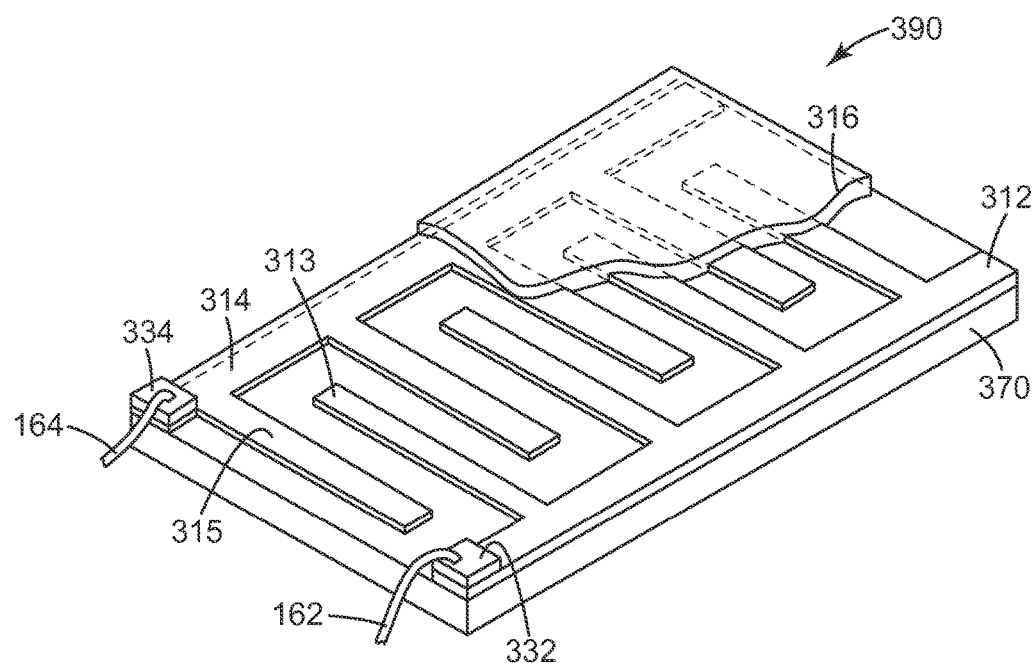
FIG. 3 is a schematic perspective view of exemplary capacitive sensor element 390.

In one embodiment, the first conductive electrode is fabricated such that it has elongated fingers that interdigitate with corresponding fingers of the second conductive electrode. Referring now to FIG. 3, capacitive sensor element 390 (one exemplary embodiment of capacitive sensor element 190 shown in FIG. 1A) comprises coplanar first and second conductive electrodes 312, 314 having respective interdigitated fingers 313, 315 disposed on dielectric base 370. Dielectric microporous material 316 is disposed over and between (i.e., at least partially between) and contacting first and second conductive electrodes 312, 314. Wires 162 and 164 connect to first and second conductive electrodes 312, 314 via respective electrically conductive bonding pads 332, 334.

Figure 4:
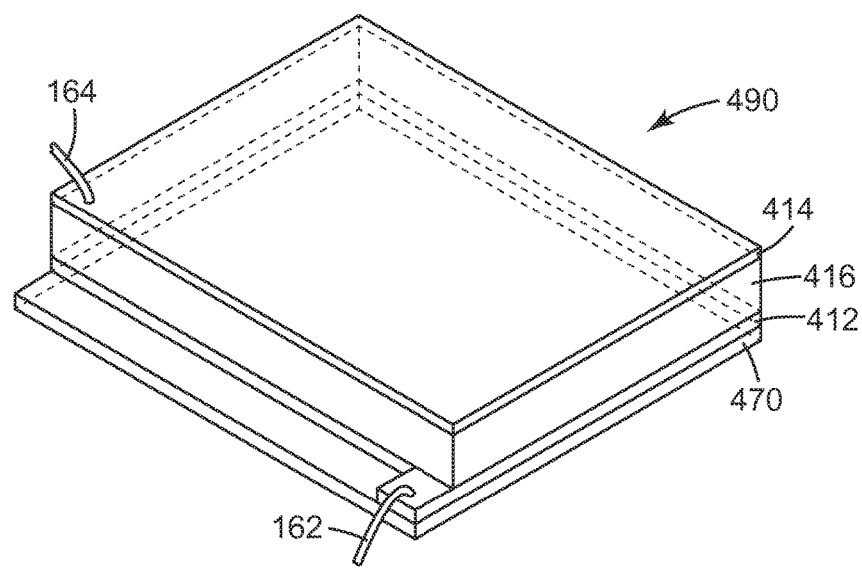
FIG. 4 is a schematic perspective view of exemplary capacitive sensor element 490.

In other embodiment, a parallel electrode configuration is used. Referring now to FIG. 4, capacitive sensor element 490 (one exemplary embodiment of capacitive sensor element 190) comprises first and second conductive electrodes 412, 414. First conductive electrode 412 is disposed on optional dielectric base 470. Dielectric microporous material 416 is disposed between and contacts first and second conductive electrodes 412, 414. Wires 162 and 164 connect to first and second conductive electrodes 412, 414.

In certain embodiments, optional dielectric base 370, 470 is omitted and a dielectric flexible base is used in its place. In these embodiments, the first and optionally second conductive electrode(s) (e.g., as in the case of capacitive sensor element 490 shown in FIG. 4) is/are deposited directly onto the flexible base.

The second conductive electrode may include additional components as long as it remains electrically conductive and optionally permeable by at least one organic analyte vapor. In the case of sensor element 110, it is highly preferable that the second conductive electrode be permeable by the analyte vapor to be detected. In the case of sensor element 310 shown in FIG. 3, the second conductive electrode may be permeable or impermeable by the analyte vapor to be detected, since it otherwise does not significantly impede the analyte from interacting with the dielectric microporous material.

Examples of materials that can be used to make the second conductive electrode include organic materials, inorganic materials, metals, alloys, and various mixtures and composites comprising any or all of these materials. In certain embodiments, coated (for example, thermal vapor coated, or sputter coated) metals or metal oxides, or combinations thereof, may be used to form the second conductive electrode such that it is permeable by organic vapors. Suitable conductive materials include for example aluminum, nickel, titanium, tin, indium-tin oxide, gold, silver, platinum, palladium, copper, chromium, carbon nanotubes, and combinations thereof. In certain embodiments, the second conductive electrode is formed by printing a silver ink, followed by drying the ink. Details concerning vapor-deposited second conductive electrodes can also be found in U.S. Pat. Appln. Publ. No. 2013/0229194 A1 (Palazzotto et al.). Combinations of different materials (conductive and/or nonconductive) can be used, as different layers or as a mixture, as long as sufficient overall conductivity and permeability is provided. Typically, the second conductive electrode has a sheet resistance of less than about $10^7$ ohms/square.

The second conductive electrode typically has a thickness in a range of from 1 nm to 100 nm, although other thicknesses may be used. For example, in some embodiments the second conductive electrode may have a thickness in a range of from 1 nm to 3000 nm, or even from 40 nm to 200 nm. Greater thicknesses may have undesirably low levels of permeability, while lesser thicknesses may become insufficiently conductive and/or difficult to electrically connect to the second conductive member. Since the second conductive electrode is permeable, the first conductive electrode typically comprises a continuous, uninterrupted layer, but it may contain openings or other interruptions if desired.

Further details concerning capacitance-related property sensors including a microporous polymer and silver ink-coated second conductive electrodes, and methods for their manufacture can be found, for example, in U.S. Pat. Appl. Publ. No. 2011/0045601 A1 (Gryska et al.), wherein both side-by-side arrangements of the first and second conductive electrodes and parallel plate electrode configurations are discussed. In that implementation, the physical thickness of the detection layer is desirably in a range of from 150 to 1200 nanometers, for example, in a range of from 500 to 900 nanometers, although thinner and thicker detection layers may also be used.

Devices and techniques for radiofrequency interrogation of capacitive sensors of the general type described above are known and have been described in col. 5, line 1 to col. 14, line 35 and corresponding Figures of U.S. Pat. No. 7,456,744 B2 (Benton et al.). In short, a radiofrequency reader is used to interrogate the sensor in the flexible sensor patch. Energy used to measure the capacitance of the sensor element is supplied by the reader. While FIGS. 1A and 1B and FIGS. 5 and 6 and the associated discussion hereinabove pertain to a passive radiofrequency device, it is also envisaged that an active radiofrequency device could be made by including a power source (e.g., a battery) that establishes a voltage difference between the first and second conductive electrodes and powers a radiofrequency transmitter. In such an embodiment, the sensor would be capable of transmitting measurements to a remote receiver (e.g., on an intermittent or continuous basis).

In some embodiments, the flexible sensor patch has conductive leads in electrical communication with the capacitive sensor element that extend at least to the boundary of the flexible sensor patch. The conductive leads can then be electrically coupled with monitoring equipment through an electrical connector assembly and/or though spring clips.

Figure 5:
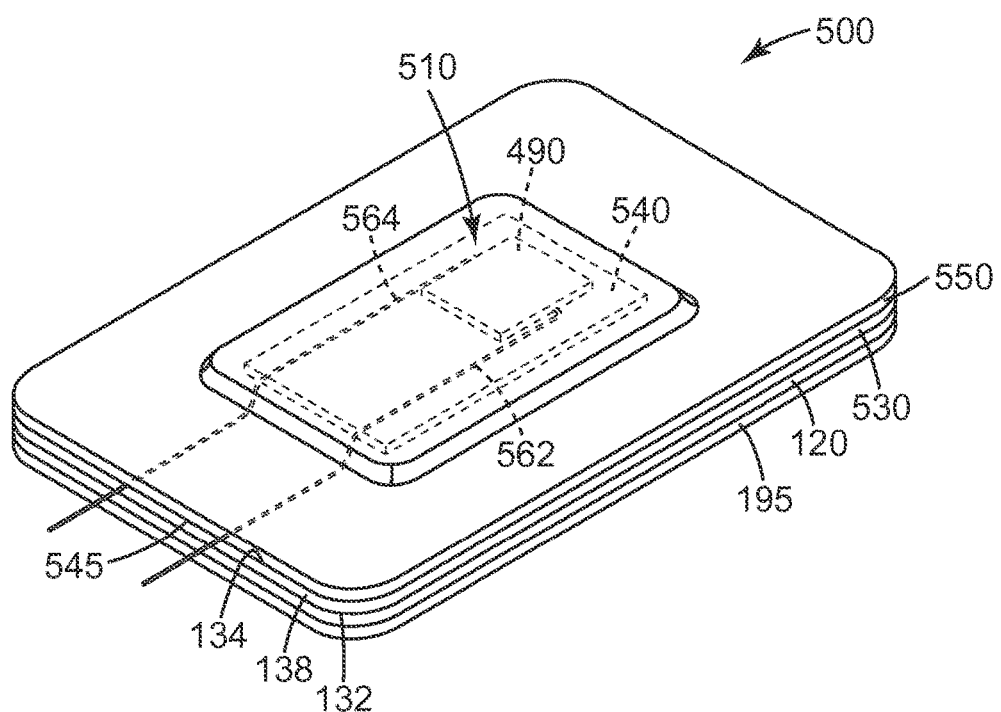
FIG. 5 is a schematic perspective view of an exemplary flexible sensor patch 500 according to the present disclosure.

Referring now to FIG. 5, flexible sensor patch 500 comprises flexible porous cover 550, sensor 510, and flexible base 530. Flexible sensor patch 500 comprises first and second conductive leads 562, 564 (e.g., wires or conductive traces) in electrical communication with respective first and second conductive electrodes of capacitive sensor element 490 (see FIG. 4). Capacitive sensor element 490 is supported on optional dielectric sensor base 540. First and second conductive leads 562, 564 contact flexible porous cover 550 and flexible base 530 along seam 545 where flexible porous cover 550 and flexible base 530 contact each other. First and second conductive leads 562, 564 extend outwardly through seam 545 beyond the periphery 138 of flexible base 530 with inner surface 134 and outer surface 132. As used herein, the term "seam" refers to a line where two components are joined together. Flexible porous cover 550 is secured to flexible base 130 enclosing sensor 510. Adhesive layer 120 is disposed on flexible base 530. Optional release layer 195 is disposed on adhesive layer 120.

Figure 6:
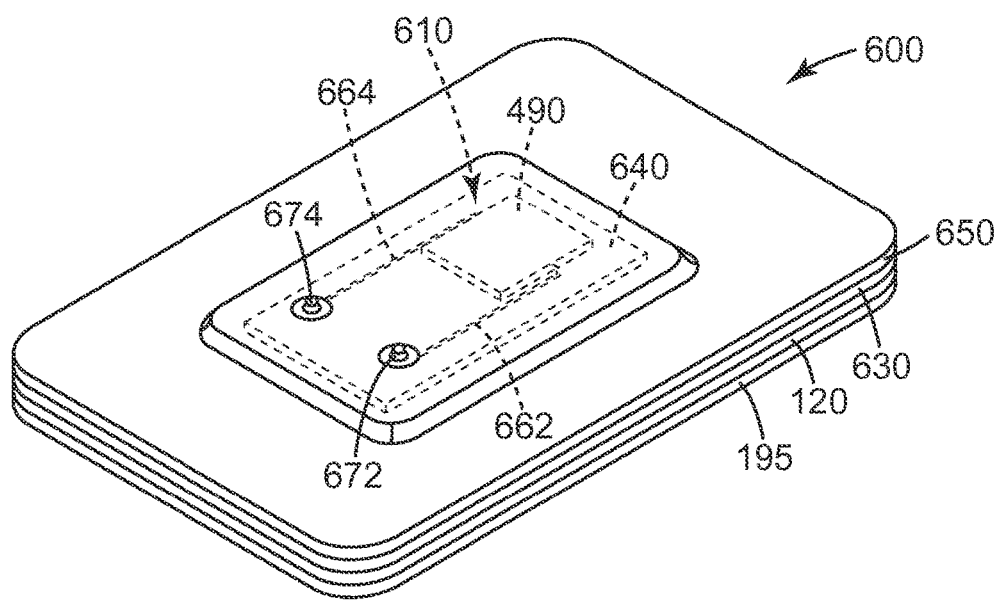
FIG. 6 is a schematic perspective view of an exemplary flexible sensor patch 600 according to the present disclosure.

In an alternative embodiment shown in FIG. 6, flexible sensor patch 600 comprises flexible porous cover 650, sensor 610, and flexible base 630. Flexible sensor patch 600 comprises first and second conductive pathways 672, 674 that extend through flexible porous cover 650 and are in electrical communication with the first and second conductive electrodes 412, 414 of capacitive sensor element 490 (see FIG. 4) via conductive leads 662, 664 (e.g., wires or conductive traces). Capacitive sensor element 490 is disposed on optional dielectric sensor base 640. Flexible porous cover 650 is secured to flexible base 630 enclosing sensor 610. Adhesive layer 120 is disposed on flexible base 630. Optional release layer 195 is disposed on adhesive layer 120.

Flexible sensor patches according to the present disclosure can be manufactured using techniques well known to those of ordinary skill in the art, and especially in view of the discussion hereinafter. In use, the flexible sensor patch is adhesively bonded to a substrate at a location where monitoring of an analyte vapor concentration is desired, and then monitored (e.g., through an electrical connection or by a radiofrequency reader (e.g., an RFID reader).

Due to their simple design and typically low cost to assemble, flexible sensor patches according to the present disclosure are suitable for use in applications where disposable sensors are desirable; for example, in medical applications where transmission of pathogens from one patient to another is to be avoided.

In one such application, flexible senor patches according to the present disclosure can be reversibly adhered to the skin of a patient near a pre-surgical site where a topical antiseptic composition has been applied. Such topical compositions often contain one or more volatile organic compounds such as, e.g., ethanol. If these organic compounds are still present when an adhesive bandage or surgical drape is applied, it may not adhere reliably to the patient's skin during the surgical procedure.

In other applications, flexible sensor patches may be advantageously adhered to irregularly or curved objects such as pipes (e.g., exterior and/or interior surface of pipes), machinery, interior surfaces ventilation ducts, and clothing.

SELECT EMBODIMENTS OF THE PRESENT DISCLOSURE

In a first embodiment, the present disclosure provides a flexible sensor patch comprising:
  a flexible base having outer and inner surfaces and a periphery;
  an adhesive layer disposed on at least a portion of the outer surface;
  a sensor comprising a capacitive sensor element, the capacitive sensor element comprising:
    a first conductive electrode;
    a second conductive electrode; and
    a dielectric microporous material disposed between the first and second conductive electrodes; and
  a flexible porous cover secured to the flexible base along at least major portion of the periphery, wherein the flexible porous cover and the flexible base collectively enclose at least a major portion of the sensor.

In a second embodiment, the present disclosure provides a flexible sensor patch according to the first embodiment, wherein the sensor further comprises a dielectric sensor base, and wherein the first conductive electrode contacts and is supported by the dielectric sensor base.

In a third embodiment, the present disclosure provides a flexible sensor patch according to the first or second embodiment, wherein the flexible porous cover and the flexible base collectively fully enclose the sensor.

In a fourth embodiment, the present disclosure provides a flexible sensor patch according to any one of the first to third embodiments, wherein the sensor comprises a radiofrequency transponder coil.

In a fifth embodiment, the present disclosure provides a flexible sensor patch according to any one of the first to third embodiments, wherein the sensor further comprises first and second conductive leads in electrical communication with the respective first and second conductive electrodes, wherein the first and second conductive leads contact the flexible porous cover and the flexible base along a seam where the flexible porous cover and the flexible base contact each other, and wherein the first and second conductive leads extend outwardly through the seam and beyond the periphery of the flexible base.

In a sixth embodiment, the present disclosure provides a flexible sensor patch according to the fifth embodiment, wherein the flexible porous cover comprises first and second conductive pathways that extend through the flexible porous cover and are in electrical communication with the first and second conductive electrodes.

In a seventh embodiment, the present disclosure provides a flexible sensor patch according to any one of the first to sixth embodiments, wherein the adhesive layer comprises a pressure-sensitive adhesive.

In an eighth embodiment, the present disclosure provides a flexible sensor patch according to any one of the first to seventh embodiments, wherein the adhesive layer is suitable for human skin contact.

In a ninth embodiment, the present disclosure provides a flexible sensor patch according to any one of the first to eighth embodiments, wherein the flexible porous cover comprises a fabric.

In a tenth embodiment, the present disclosure provides a flexible sensor patch according to any one of the first to ninth embodiments, wherein the flexible base comprises at least one of fabric or a polymer film.

In an eleventh embodiment, the present disclosure provides a method of monitoring organic vapor concentration proximate to a substrate, the method comprising:
providing a flexible sensor patch according to any one of the first to tenth embodiments, adhesively bonding the adhesive layer to a substrate;
establishing a voltage difference between the first and second conductive electrodes; and
obtaining a capacitance-related property of the sensor.

In a twelfth embodiment, the present disclosure provides a method according to the eleventh embodiment, wherein the substrate comprises patient skin near a pre-surgical skin site.

All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A flexible sensor patch comprising:
a flexible base having outer and inner surfaces and a periphery;
an adhesive layer disposed on at least a portion of the outer surface;
a sensor comprising a capacitive sensor element disposed on the inner surface of the flexible base, the capacitive sensor element comprising:
a first conductive electrode;
a second conductive electrode; and
a dielectric microporous material disposed between the first and second conductive electrodes; and
a flexible porous cover secured to the flexible base along at least major portion of the periphery,
wherein the sensor further comprises a radiofrequency transponder disposed on the inner surface of the flexible base, adjacent to the capacitive sensor element and electrically coupled with the capacitive sensor element,
wherein the first conductive electrode of the capacitive sensor element is disposed on the inner surface of the flexible base, coplanar with the radiofrequency transponder, and surrounded by the radiofrequency transponder, and
wherein the flexible porous cover and the flexible base collectively enclose at least a major portion of the capacitive sensor element and the radiofrequency transponder.

2. The flexible sensor patch of claim 1, wherein the sensor further comprises a dielectric sensor base, and wherein the first conductive electrode contacts and is supported by the dielectric sensor base.

3. The flexible sensor patch of claim 1, wherein the flexible porous cover and the flexible base collectively fully enclose the sensor.

4. The flexible sensor patch of claim 1, wherein the sensor further comprises first and second conductive leads in electrical communication with the respective first and second conductive electrodes, wherein the first and second conductive leads contact the flexible porous cover and the flexible base along a seam where the flexible porous cover and the flexible base contact each other, and wherein the first and second conductive leads extend outwardly through the seam and beyond the periphery of the flexible base.

5. The flexible sensor patch of claim 4, wherein the flexible porous cover comprises first and second conductive pathways that extend through the flexible porous cover and are in electrical communication with the first and second conductive electrodes.

6. The flexible sensor patch of claim 1, wherein the adhesive layer comprises a pressure-sensitive adhesive.

7. The flexible sensor patch of claim 1, wherein the adhesive layer is suitable for human skin contact.

8. The flexible sensor patch of claim 1, wherein the flexible porous cover comprises a fabric.

9. The flexible sensor patch of claim 1, wherein the flexible base comprises at least one of fabric or a polymer film.

10. A method of monitoring organic vapor concentration proximate to a substrate, the method comprising:
providing a flexible sensor patch according to claim 1, adhesively bonding the adhesive layer to a substrate;
establishing a voltage difference between the first and second conductive electrodes; and
obtaining a capacitance-related property of the sensor.

11. The method of claim 10, wherein the substrate comprises patient skin near a pre-surgical skin site.

12. The flexible sensor patch of claim 1, wherein the radiofrequency transponder and the capacitive sensor element are formed directly on the flexible base.

13. The flexible sensor patch of claim 1, wherein the dielectric microporous material covers at least a portion of the radiofrequency transponder.

* * * * *